United States Patent [19]
Higa

[11] Patent Number: 4,696,813
[45] Date of Patent: Sep. 29, 1987

[54] MELANIN INHIBITING COSMETIC COMPOSITION

[75] Inventor: Yoshitaka Higa, Dazaifu, Japan

[73] Assignee: Sansho Seiyaku Co., Ltd., Fukuoka, Japan

[21] Appl. No.: 751,755

[22] Filed: Jul. 3, 1985

[51] Int. Cl.$^4$ ............... A61K 7/021; A61K 35/50; A61K 35/84
[52] U.S. Cl. ................................ 424/59; 424/62; 424/63; 424/95; 424/195.1; 514/21; 514/844
[58] Field of Search ........... 424/195.1, 95, 59, 62–64; 514/844, 21; 530/851

[56] References Cited

U.S. PATENT DOCUMENTS 4,278,656  7/1981  Nagai et al. .................... 424/59

OTHER PUBLICATIONS

Chem. Abstracts Citation of JP 81 44,046, vol. 96, 1982, No. 129592f, (Ichimaru Co. Ltd.).

Primary Examiner—Johnnie R. Brown
Assistant Examiner—Jacqueline M. Stone
Attorney, Agent, or Firm—Jordan and Hamburg

[57] ABSTRACT

Placenta extracts and kojic acid or kojic acid derivatives are formulated into cosmetic bases to make cosmetic compositions. The cosmetic compositions exhibit an enhanced whitening effect for the skin due to the action of the placenta extract and kojic acid or kojic acid derivatives.

4 Claims, No Drawings

MELANIN INHIBITING COSMETIC COMPOSITION

BACKGROUND OF THE INVENTION

1. Field of the Invention

The present invention relates to cosmetic compositions and, more particularly to whitening cosmetic compositions for enhancing a whitening effect of the skin.

2. Brief Description of the Prior art

A variety of whitening cosmetics have been proposed or investigated and developed in order to remove spots such as stains, freckles, etc. appearing on the skin and to exhibit a whitening effect on the skin as a whole.

In the past, peroxides such as hydrogen peroxide, zinc peroxide, magnesium peroxide, sodium peroxide, zinc perborate, etc. were formulated in cosmetic compositions. However, these peroxides involve difficulties in storability and adaptability to formulating them in cosmetics because they are extremely unstable substances. Further, their whitening effect was unsatisfactory. Then, cosmetics in which vitamin C, cystein, colloidal sulfur, etc. are formulated were employed but they were still unsatisfactory.

In recent days, it has been reported that kojic acid obtained by cultivation of bacteria such as koji mold, etc. has an effect of rendering the skin fair as a whitening component for the whitening cosmetics. Whitening cosmetic using kojic acid are known in, for example, Published Examined Japanese Patent Application No. 18569/81 and Published Unexamined Japanese Patent Application No. 3538/78. Further, derivatives of kojic acid have been investigated and cosmetics containing kojic acid derivatives are known, for example, as shown in Published Unexamined Japanese Patent Application Nos. 7710/81, 7776/81 and 79616/81. Furthermore cosmetics containing pyrone compounds, chromone compounds or flavonol compounds are known, for example, as shown in Published Unexamined Japanese Patent Application Nos. 3538/78, 92305/80, 111410/80, 111411/80, 143908/80, 157580/80, 14517/82, 35506/82, 131911/83, etc.

Further, cosmetics in which placenta extracts are formulated are disclosed, for example, in Published Examined Japanese Patent Application No. 15399/60.

SUMMARY OF THE INVENTION

The present invention is concerned with cosmetic compositions comprising formulations of placenta extracts and kojic acid or derivatives thereof in cosmetic bases. The cosmetic composition is a whitening cosmetic composition having an extremely excellent whitening effect which is exhibited by the placenta extract and kojic acid or derivatives thereof having different mechanisms on tyrosinase which participates in the initial stage of melanine formation.

DETAILED DESCRIPTION OF THE INVENTION

The placenta extracts which are employed in the present invention are aqueous solutions obtained by extracting water-soluble portions with water via means of washing placenta of human or animals such as cows, etc., withdrawing blood therefrom, crushing, freezing, etc. and, further removing impurities from the extract. The thus obtained extracts are commercially available as placenta extracts and used mainly as raw materials for cosmetics. These placenta extracts may be any of those derived from human and derived from animals such as cows, etc. but the human-derived placenta extracts are preferred.

An exemplary mode of preparing a human placenta extract suitable for use in the present invention, as disclosed in Published Examined Japanese Patent Application No. 15399/60, comprises: (A) sterilizing and then removing blood from human placenta, washing with a physiological saline solution and freezing; (B) destroying the constituent cell wall; (C) heating the exduded cell liquid at 80°-100° C., removing the precipitate and then removing precipitate by centrifugation; (D) sterilizing the supernatant liquid and allowing in a cool and dark room after separating the precipitate with ethanol; (E) vacuum drying the precipitate and dissolving with distilled water; and (F) separating the solution by centrifugation and collecting the placentin.

Examples of the kojic acid derivatives used in the present invention include monofatty acid esters of kojic acid, for example, kojic acid monopalmitate, kojic acid monobutyrate, kojic acid monocaprylate and kojic acid monostearate (disclosed in Published Unexamined Japanese Patent Application No. 77272/81); difatty acid esters of kojic acid, for example, kojic acid dipalmitate, kojic acid dibutyrate, kojic acid dioleate and kojic acid distearate (disclosed in Published Unexamined Japanese Patent Application No. 7776/81); and, in addition thereto, kojic acid monocinnamoate, kojic acid monobenzoate, etc. (disclosed in Published Unexamined Japanese Patent Application No. 33207/84).

An exemplary mode of preparing kojic acid suitable for use in the present invention, as disclosed in Published Examined Japanese Patent Application No. 18569/81, comprised fermenting fungi belonging to such generics as aspergillus, penicillium, gluconobacter and the like to obtain a product containing kojic acid as the main component, along with saccharide, peptides, amino acids and the like.

As to the kojic acid derivatives suitable for use in the present invention and, for example, so disclosed in Published Unexamined Japanese Patent Application No. 77272/81, kojic acid monopalmitate, monobutyrate, momocaprylate, etc. may be prepared by adding a chloride of an aliphatic carboxylic acid to pyridine solution of kojic acid, esterifying the kojic acid at room temperature and separating the esterification product through chromatography or extraction with an organic solvent. Similarly, as disclosed in Published Unexamined Japanese Patent Appliction No. 7776/81, diesterified compounds of kojic acid, said such as kojic acid dipalmatate, may be prepared by esterifying a solution of kojic acid in pyridine with a chloride of a fatty carboxylic acid such as butyric acid, oleic acid, etc., at room temperature.

The ratios of the above placenta extract and kojic acid or kojic acid derivatives are that the kojic acid and or kojic acid derivatives are in a range of 0.1-3 (by weight) based on the placenta extract 10 (weight).

The ratios of these effective components to be contained in the cosmetic composition are that the placenta extract is in the range of approximately 0.1 to 10% (by weight) based on the total amount of cosmetic composition and kojic acid or kojic acid derivatives are in a range of approximately 0.1 to 3% (by weight) based on the total cosmetic composition. By these ratios, the effect can be sufficiently exhibited.

The cosmetic composition of the present invention is applicable mainly as cosmetics for the skin such as lotion, cream, emulsion, pack, etc. and, the placenta extract and kojic acid or kojic acid derivatives are incorporated into cosmetic bases, aids, etc. conventionally used for these cosmetics to make the cosmetic compositions.

For example, with respect to lotions, in a process for producing conventional lotions which comprises dissolving moisturizing agents, skin nutrients or the like, such as glycerin, propylene glycol, etc., in purified water, on one hand, and on the other hand, dissolving preservatives, aromatics, etc. in alcohols, mixing both solutions and solubilizing them at room temperature, the placenta extract and kojic acid or kojic acid derivatives which are effective components of the present invention are incorporated into water-soluble portions to make lotions.

With respect to creams, in a process for producing conventional creams which comprises incorporating hydrophilic components, for example, moisturizing agents such as glycerin, sorbitol, etc., into purified water to make an aqueous phase portion; incorporating, as an oily phase portion, oily components such as preservatives, surface active agents, etc. into solid oils such as beeswax, paraffin, microcrystalline wax, ceresine, higher fatty acids, hardened oils, etc., semi-solid oils such as vaseline, lanoline, glycerides, etc., and liquid oils such as squalane, liquid paraffin, various ester oils, etc. to control, warming the thus obtained aqueous phase portion and, gradually adding the oily phase portion warmed at the same temperature to the aqueous phase portion while mildly stirring to emulsify them, the placenta extract and kojic acid or kojic acid derivatives which are effective components of the present invention are incorporated into the aqueous phase portion to make creams.

With respect to emulsions, in a process for producing conventional emulsions which comprises incorporating moisturizing agents such as glycerin, etc. or pH controlling agents such as acids or alkalis to purified water, mixing them with heating, adding ethanol to the mixture to make an aqueous phase portion; on the other hand, incorporating oily components such as preservatives, surface active agents, etc. into solid oils such as beeswax, paraffin, etc., semi-solid oils such as vaseline, lanoline, etc., and liquid oils such as squaline, liquid paraffin, various ester oils, etc. to control, mixing them with heating to make an oily phase portion, adding the oily phase portion to the aqueous phase portion to perform preliminary emulsification, adding protective colloids such as carboxyvinyl polymer, carboxylmethyl cellulose, etc. to the emulsion, and homogeneously emulsifying them with a homomixer to make emulsions, to the placenta extract and kojic acid or kojic acid derivatives which are effective components of the present invention are incorporated into the aqueous phase portion to make emulsions.

With respect to facial packs, in a process for producing conventional facial packs which comprises incorporating moisturizing agents such as glycerin, etc,. film-forming agents such as polyvinyl alcohol, bee gum, etc. into purified water to swell adding powders such as kaolin, talc, zinc oxide, etc., if necessary, and adding ethanol having dissolved therein aromatics, preservatives, etc. thereto to knead to a paste form, the placenta extract and kojic acid or kojic acid derivatives which are effective components of the present invention are incorporated into the aqueous phase portion to make facial packs.

The whitening effect exhibited by the use of the placenta extract and kojic acid or kojic acid derivatives in combination which are effective components of the present invention is synergistic and excellent as compared to the same effect exhibited by the use of each component alone.

The foregoing effect is demonstrated by decoloration test using incubated chromocyte.

Text Example

1. Cell used
   Mouse melanoma B 16 cell (hereinafter B 16 cell)
2. Conditions for incubation
   Using Eagle's MEM medium supplemented with 10% bovine fetal serum, 2.2 g/1 of hydrogen sodium carbonate and 5 mM N-2-hydroxyethylpiperazine-N'-ethanesulfonic acid, incubation was preformed in a $CO_2$ incubator set at 37° C. in 5% of $CO_2$.
3. Test Fractions
   Fraction A: fraction to which neither kojic acid nor the placenta extract was added.
   Fraction B: fraction to which kojic acid was added.
   0.1 mM was added to Fraction B-I;
   0.5 mM was added to Fraction B-II;
   1.0 mM was added to Fraction B-III;
   2.0 mM was added to Fraction B-VI;
   3.0 mM was added to Fraction B-V.
   Fraction C: fraction to which the placenta extract was added. After freeze drying 100 ml of the placenta extract, this was dissolved in 100 ml of cell culture solution; the thus obtained solution was used as a raw solution.
   1/16 volume of the raw solution was added to Fraction C-I;
   ⅛ volume of the raw solution was added to Fraction C-II;
   ¼ volume of the raw solution was added to Fraction C-III;
   ½ volume of the raw solution was added to Fraction C-IV; the raw solution was added to Fraction C-V.
   Fraction D: fraction which kojic acid and the placenta extract which were effective components of the present invention were used in combination.
   0.1 mM of kojic acid and 1/16 volume of the raw solution of the placenta extract were used in combination for Fraction D-I;
   0.5 mM of kojic acid and ⅛ volume of the raw solution of the placenta extract were used in combination for Fraction D-II;
   1.0 mM of kojic acid and ¼ volume of the raw solution of the placenta extract were used in combination for Fraction D-III;
   2.0 mM of kojic acid and ½ volume of the raw solution of the placenta extract were used in combination for Fraction D-IV ;
   3.0 mM of kojic acid and the raw solution of the placenta extract were used in combination for Fraction D-V.
4. Evaluation of inhibitory action against formation of melanine.

On each test fraction, $1.2 \times 10^5$ cells/dish of B 16 cells were inoculated. After incubating for 6 days, proliferated cells were dispersed with trypsin and then collected by centrifugal separation at 1000 r.p.m. ×5 minutes. The blackening degree was evaluated with the naked eye.
- —: The blackening degree was almost the same as that of the fraction to which nothing was added.
- ±: The blackening degree was somewhat less than that of the fraction to which nothing was added.
- +: The blackening degree was obviously less than that of The fraction to which nothing was added.
- ++: the blackening degree was slightly noted.
- +++: The color was white to gray but no blackening was noted.

5. Results of evaluation

The results are shown in the table below.

| Fraction | I | II | III | IV | V |
|---|---|---|---|---|---|
| A | − | − | − | − | − |
| B | − | − | + | + | ++ |
| C | − | − | ± | + | ++ |
| D | + | ++ | +++ | +++ | +++ |

As is evident from the above results, the effective components of the present invention provide marked inhibitory effect against the formation of melanine, not only as compared to the fraction to which nothing was added but also as compared to the fraction to which one of the effective components of the present invention was added alone.

It is known that kojic acid or kojic acid derivatives and the placenta extract which are the effective components of the present invention have the action of inhibiting the formation of melanine, respectively, even by single use. However, by investigations of the present inventors, it has been proved that as a result of analysis on the mechanism of inhibiting the formation of melanine in cell line using B 16 cells used in this test, kojic acid forms a chelation with copper ions which affect the activity of tyrosinase that takes part in the formation of melanine at the initial stage thereby to prevent tyrosinase activity and inhibit the formation of melanine; whereas, the placenta extract does not chelate with the copper ions but the mechanism of the placenta extract on preventing the formation of melanine is different from that of kojic acid. As a result, the synergistic effect of both kojic acid or kojic acid derivatives and the placenta extract is believed to be exhibited by the different actions of inhibiting the formation of melanine.

EXAMPLES

Next, the present invention is explained referring to the examples.

EXAMPLE 1

(Cream)

Kojic acid—1.0%
Placenta extract—5.0%
Polyoxyethylene stearyl ether—2.09%
Polyoxyethylene cetyl ether—2.91%
Beeswax—4.0%
Cetanol—3.0%
Isopropyl palmitate—2.0%
Liquid paraffin—15.0%
Polyethylene glycol monostearate—0.5%
Purified water—64.4%
Methyl p-oxybenzoate—0.1%

EXAMPLE 2

(Emulsion)

Kojic acid—2.0%
Placenta extract—4.0%
Self-emulsified tylpe glycerol monostearate—1.11%
Polyoxyethylene cetyl ether—1.89%
MC stearic acid—2.0%
Cetanol—1.0%
Isopropyl myristate—2.0%
Purified water—85.90%
p-Oxybenzoic acid—0.1%
Aromatics—trace

EXAMPLE 3

(Facial Pack)

Kojic acid—0.5%
Placenta extract—6.0%
Ethanol—3.0%
Methyl p-oxybenzoate—0.1%
Carboxyvinyl polymer—1.0%
Calcium carbonate—0.3%
Titanium dioxide—0.02%
Purified water—89.08%
Aromatics—trace

EXAMPLE 4

(Lotion)

Kojic acid—3.0%
Placenta extract—10.0%
Ethanol—10.0%
Methyl p-oxybenzoate—0.1%
Citric acid—0.2%
Aromatics—trace
Purified water—76.7%

While the invention has been described in detail and with reference to specific embodiments thereof, it will be apparent to one skilled in the art that various changes and modifications can be made therein without departing from the spirit and scope thereof.

What is claimed is:

1. A cosmetic composition for inhibiting the formation of melanine comprising placentin and kojic acid, wherein the weight ratio of kojic acid to placentin ranges from about 0.1:10 to about 3:10.

2. A cosmetic composition as in claim 1, wherein the placentin is extracted from human placenta.

3. A cosmetic composition as in claim 1, wherein the placentin is extracted from animal placenta.

4. A cosmetic composition as in claim 1, wherein the placentin is present in amount ranging from about 0.1 to about 10 percent by weight of the cosmetic composition and the kojic acid is present in an amount ranging from about 0.1 to about 3 percent by weight of the cosmetic composition.

* * * * *